United States Patent
Rauker et al.

(10) Patent No.: US 9,301,829 B2
(45) Date of Patent: Apr. 5, 2016

(54) EMBOLIC PROTECTION ASPIRATOR

(75) Inventors: Robert M. Rauker, Ashland, MA (US); William J. Shaw, Cambridge, MA (US); James G. Hansen, Coon Rapids, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2900 days.

(21) Appl. No.: 10/630,308

(22) Filed: Jul. 30, 2003

(65) Prior Publication Data
US 2005/0033347 A1 Feb. 10, 2005

(51) Int. Cl.
*A61M 29/00* (2006.01)
*A61F 2/01* (2006.01)

(52) U.S. Cl.
CPC ........... *A61F 2/013* (2013.01); *A61F 2002/015* (2013.01); *A61F 2002/018* (2013.01); *A61F 2230/0006* (2013.01); *A61F 2230/008* (2013.01); *A61F 2230/0067* (2013.01); *A61F 2230/0069* (2013.01)

(58) Field of Classification Search
USPC ........................................................ 606/200
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |

(Continued)

FOREIGN PATENT DOCUMENTS

| | | |
|---|---|---|
| DE | 28 21 048 | 7/1980 |
| DE | 34 17 738 | 11/1985 |

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).
"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).

(Continued)

*Primary Examiner* — Richard Louis
(74) *Attorney, Agent, or Firm* — Seager, Tufte & Wickhem LLP

(57) ABSTRACT

Embolic protection aspirators and methods for extracting debris from the vasculature during interventional procedures are provided. One such system may include an aspirating filter delivery catheter having a filtration device, an operable end cap, and a plurality of aspiration ports. The delivery catheter may be fluidly coupled to a suction providing means for extracting debris while traversing a target site for distal delivery of the filtration device. Another such system may include an aspirating filter retrieval catheter having an aspiration lumen and a balloon. The aspiration lumen may be fluidly coupled to a suction providing means for extracting debris from the filtration device prior to and/or during retrieval of the filtration device. By inflating the balloon to partially or fully restrict blood flow, suction pressure proximal of the filtration device may be increased to enhance debris extraction.

16 Claims, 7 Drawing Sheets

(56) References Cited

U.S. PATENT DOCUMENTS

| | | | |
|---|---|---|---|
| 4,790,812 | A | 12/1988 | Hawkins, Jr. et al. |
| 4,790,813 | A | 12/1988 | Kensey |
| 4,794,928 | A | 1/1989 | Kletschka |
| 4,807,626 | A | 2/1989 | McGirr |
| 4,867,156 | A * | 9/1989 | Stack et al. .................. 606/159 |
| 4,873,978 | A | 10/1989 | Ginsburg |
| 4,921,478 | A | 5/1990 | Solano et al. |
| 4,921,484 | A | 5/1990 | Hillstead |
| 4,926,858 | A | 5/1990 | Gifford, III et al. |
| 4,969,891 | A | 11/1990 | Gewertz |
| 4,998,539 | A | 3/1991 | Delsanti |
| 5,002,560 | A | 3/1991 | Machold et al. |
| 5,011,488 | A | 4/1991 | Ginsburg |
| 5,053,008 | A | 10/1991 | Bajaj |
| 5,071,407 | A | 12/1991 | Termin et al. |
| 5,100,423 | A | 3/1992 | Fearnot |
| 5,102,415 | A | 4/1992 | Guenther et al. |
| 5,133,733 | A | 7/1992 | Rasmussen et al. |
| 5,152,771 | A | 10/1992 | Sabbaghian et al. |
| 5,152,777 | A | 10/1992 | Goldberg et al. |
| 5,160,342 | A | 11/1992 | Reger et al. |
| 5,224,953 | A | 7/1993 | Morgentaler |
| 5,329,942 | A | 7/1994 | Gunther et al. |
| 5,330,484 | A | 7/1994 | Gunther |
| 5,354,310 | A | 10/1994 | Garnie et al. |
| 5,376,100 | A | 12/1994 | Lefebvre |
| 5,421,832 | A | 6/1995 | Lefebvre |
| 5,423,742 | A | 6/1995 | Theron |
| 5,449,372 | A | 9/1995 | Schmaltz et al. |
| 4,842,579 | B1 | 10/1995 | Shiber |
| 5,456,667 | A | 10/1995 | Ham et al. |
| 5,462,529 | A | 10/1995 | Simpson et al. |
| 5,536,242 | A | 7/1996 | Willard et al. |
| 5,549,626 | A | 8/1996 | Miller et al. |
| 5,658,296 | A | 8/1997 | Bates et al. |
| 5,662,671 | A | 9/1997 | Barbut et al. |
| 5,695,519 | A | 12/1997 | Summers et al. |
| 5,720,764 | A | 2/1998 | Naderlinger |
| 5,728,066 | A | 3/1998 | Daneshvar |
| 5,749,848 | A | 5/1998 | Jang et al. |
| 5,769,816 | A | 6/1998 | Barbut et al. |
| 5,779,716 | A | 7/1998 | Cano et al. |
| 5,792,157 | A | 8/1998 | Mische et al. |
| 5,795,322 | A | 8/1998 | Bouewijn |
| 5,800,457 | A | 9/1998 | Gelbfish |
| 5,800,525 | A | 9/1998 | Bachinski et al. |
| 5,810,874 | A | 9/1998 | Lefebvre |
| 5,814,064 | A | 9/1998 | Daniel et al. |
| 5,827,324 | A | 10/1998 | Cassell et al. |
| 5,833,644 | A | 11/1998 | Zadno-Azizi et al. |
| 5,833,650 | A | 11/1998 | Imran |
| 5,846,260 | A | 12/1998 | Maahs |
| 5,848,964 | A | 12/1998 | Samuels |
| 5,876,367 | A | 3/1999 | Kaganov et al. |
| 5,895,399 | A | 4/1999 | Barbut et al. |
| 5,910,154 | A | 6/1999 | Tsugita et al. |
| 5,911,734 | A | 6/1999 | Tsugita et al. |
| 5,925,016 | A | 7/1999 | Chornenky et al. |
| 5,925,060 | A | 7/1999 | Forber |
| 5,925,062 | A | 7/1999 | Purdy |
| 5,935,139 | A | 8/1999 | Bates |
| 5,941,869 | A | 8/1999 | Patterson et al. |
| 5,941,896 | A | 8/1999 | Kerr |
| 5,947,995 | A | 9/1999 | Samuels |
| 5,954,745 | A | 9/1999 | Gertler et al. |
| 5,980,555 | A | 11/1999 | Barbut et al. |
| 5,989,281 | A | 11/1999 | Barbut et al. |
| 5,993,469 | A | 11/1999 | McKenzie et al. |
| 5,997,557 | A | 12/1999 | Barbut et al. |
| 6,001,118 | A | 12/1999 | Daniel et al. |
| 6,007,557 | A | 12/1999 | Ambrisco et al. |
| 6,010,522 | A | 1/2000 | Barbut et al. |
| 6,013,085 | A | 1/2000 | Howard |
| 6,027,520 | A | 2/2000 | Tsugita et al. |
| 6,042,598 | A | 3/2000 | Tsugita et al. |
| 6,051,014 | A | 4/2000 | Jang |
| 6,051,015 | A | 4/2000 | Maahs |
| 6,053,932 | A | 4/2000 | Daniel et al. |
| 6,059,814 | A | 5/2000 | Ladd |
| 6,066,149 | A | 5/2000 | Samson et al. |
| 6,066,158 | A | 5/2000 | Engelson et al. |
| 6,068,645 | A | 5/2000 | Tu |
| 6,086,605 | A | 7/2000 | Barbut et al. |
| 6,117,154 | A | 9/2000 | Barbut et al. |
| 6,129,739 | A | 10/2000 | Khosravi |
| 6,135,991 | A | 10/2000 | Muni et al. |
| 6,136,016 | A | 10/2000 | Barbut et al. |
| 6,142,987 | A | 11/2000 | Tsugita |
| 6,152,909 | A | 11/2000 | Bagaoisan et al. |
| 6,152,946 | A * | 11/2000 | Broome et al. ............... 606/200 |
| 6,152,947 | A | 11/2000 | Ambrisco et al. |
| 6,165,200 | A | 12/2000 | Tsugita et al. |
| 6,168,579 | B1 * | 1/2001 | Tsugita ..................... 604/96.01 |
| 6,171,327 | B1 | 1/2001 | Daniel et al. |
| 6,171,328 | B1 | 1/2001 | Addis |
| 6,179,851 | B1 | 1/2001 | Barbut et al. |
| 6,179,859 | B1 | 1/2001 | Bates et al. |
| 6,179,861 | B1 | 1/2001 | Khosravi et al. |
| 6,203,561 | B1 * | 3/2001 | Ramee et al. ................. 606/200 |
| 6,206,868 | B1 | 3/2001 | Parodi |
| 6,214,026 | B1 | 4/2001 | Lepak et al. |
| 6,221,006 | B1 | 4/2001 | Dubrul et al. |
| 6,224,620 | B1 | 5/2001 | Maahs |
| 6,231,544 | B1 | 5/2001 | Tsugita et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,245,087 | B1 | 6/2001 | Addis |
| 6,245,088 | B1 | 6/2001 | Lowery |
| 6,245,089 | B1 | 6/2001 | Daniel et al. |
| 6,258,115 | B1 | 7/2001 | Dubrul |
| 6,264,663 | B1 | 7/2001 | Cano |
| 6,264,672 | B1 | 7/2001 | Fisher |
| 6,270,477 | B1 | 8/2001 | Bagaoisan et al. |
| 6,270,513 | B1 | 8/2001 | Tsugita et al. |
| 6,277,138 | B1 | 8/2001 | Levinson et al. |
| 6,277,139 | B1 | 8/2001 | Levinson et al. |
| 6,280,413 | B1 | 8/2001 | Clark et al. |
| 6,287,321 | B1 | 9/2001 | Jang |
| 6,290,710 | B1 | 9/2001 | Cryer et al. |
| 6,306,163 | B1 | 10/2001 | Fitz |
| 6,309,399 | B1 | 10/2001 | Barbut et al. |
| 6,319,268 | B1 | 11/2001 | Ambrisco et al. |
| 6,344,049 | B1 | 2/2002 | Levinson et al. |
| 6,346,116 | B1 * | 2/2002 | Brooks et al. ................. 606/200 |
| 6,398,775 | B1 * | 6/2002 | Perkins et al. ................ 604/514 |
| 6,406,471 | B1 | 6/2002 | Jang et al. |
| 6,511,492 | B1 * | 1/2003 | Rosenbluth et al. .......... 606/159 |
| 6,544,276 | B1 | 4/2003 | Azizi |
| 6,569,148 | B2 | 5/2003 | Bagaoisan et al. |
| 6,596,011 | B2 | 7/2003 | Johnson et al. |
| 6,610,005 | B1 * | 8/2003 | Tao ................................. 600/34 |
| 6,849,068 | B1 * | 2/2005 | Bagaoisan et al. ............. 604/523 |
| 7,169,165 | B2 * | 1/2007 | Belef et al. ..................... 606/200 |
| 2002/0123761 | A1 | 9/2002 | Pastrone et al. |
| 2003/0023227 | A1 | 1/2003 | Zadno-Azizi et al. |
| 2003/0097094 | A1 * | 5/2003 | Ouriel et al. ................ 604/93.01 |
| 2003/0176886 | A1 * | 9/2003 | Wholey et al. ................ 606/200 |
| 2004/0006370 | A1 * | 1/2004 | Tsugita ......................... 606/200 |
| 2005/0004594 | A1 * | 1/2005 | Nool et al. .................... 606/200 |

FOREIGN PATENT DOCUMENTS

| | | |
|---|---|---|
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 630 617 A1 | 6/1993 |

(56) References Cited

FOREIGN PATENT DOCUMENTS

| | | |
|---|---|---|
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/35858 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

EMBOLIC PROTECTION ASPIRATOR

FIELD OF THE INVENTION

The present invention generally relates to intravascular devices used in interventional procedures. More specifically, the present invention relates to systems and methods for extracting debris, e.g., emboli, thrombi, etc., during the placement and retrieval of a blood permeable filtration device.

BACKGROUND OF THE INVENTION

Vascular procedures such as angioplasty, atherectomy, thrombectomy, stent placement, etc., used for treating occlusive vascular diseases cause material to dislodge from the inside wall of blood vessels and enter the bloodstream. The dislodged material (e.g., plaque), known as emboli, may be sufficiently large to occlude downstream blood vessels, potentially blocking blood flow to tissue. Additionally, blood clots, known as thrombi, may form and either be sufficiently large or grow over time and block a blood vessel should the thrombus become released into the bloodstream.

Numerous interventional systems and methods that employ a filtration device designed to capture debris during the treatment or diagnosis of vascular disease are well known in the art. The procedure typically involves using a filter delivery catheter to transluminally insert and deliver, within a blood vessel, a filtration device to a location distal of a target site, such as a stenosis or a lesion, and then deploying the filter causing it to open. During such filter delivery process, plaque could be liberated from the walls of the blood vessel and create emboli and thrombi that may enter the bloodstream and potentially occlude distal blood vessels.

After deploying the blood permeable filtration device distal of the target site, an interventional device may be delivered over the guide wire to the target site. During treatment of a stenosis or a lesion within the blood vessel, plaque may be liberated from the walls of the blood vessel creating emboli and thrombi. This debris could then be entrapped in the distally deployed filter, and hinder its removal from the vasculature.

In view of the foregoing, it is desirable to provide an aspirating filter delivery catheter and method for extracting debris during the filter delivery process. It is further desirable to provide an aspirating filter retrieval catheter for extracting debris accumulated proximal of the filter prior to extracting the filter from the vasculature.

SUMMARY OF THE INVENTION

The present invention pertains to an aspirating filter delivery catheter deployable in a blood vessel for extracting debris resulting from the filter delivery catheter traversing the target site, such as a stenosis or a lesion. In one embodiment of the invention, the aspirating filter delivery catheter may include a blood permeable filtration device located within the elongated shaft proximate the distal end of the shaft, and one or more aspiration ports located circumferentially and/or longitudinally on the elongated shaft proximate the distal end of the shaft and proximal of the filtration device.

In an alternate embodiment, the aspirating filter delivery catheter may further include an operable end cap at the distal opening of the elongated shaft for minimizing debris collection on the distal side of the filter while the catheter is being advanced to the target site.

The filter delivery catheter may be slidably coupled to a guide wire, and suction may be applied to the proximal end of the elongated shaft for extracting, through the aspiration ports, debris resulting from the distal region of the delivery catheter traversing the target site, such as a stenosis or a lesion.

The present invention also pertains to an aspirating filter retrieval catheter deployable in a blood vessel for extracting debris entrapped on the proximal side of the blood permeable filter to enable collapsing the filter for removal. In one embodiment of the invention, the aspirating filter retrieval catheter may include an elongated shaft having an aspiration lumen traversing the length of the shaft, and also having a short guide wire lumen proximate the distal end of the shaft. The guide wire lumen could be in fluid communication with the aspiration lumen and the lumen of the blood vessel. The guide wire lumen may be used for slidably coupling the filter retrieval catheter to the guide wire, and the distal end of the catheter may be advanced to a region proximal of the filter. Suction may then be applied to the proximal end of the aspiration lumen of the elongated shaft for extracting debris entrapped on the proximal side of the filter.

In an alternate embodiment, the aspirating filter retrieval catheter may further include an inflatable balloon around the elongated shaft proximate the distal end of the shaft. The balloon may be fluidly coupled to an inflation/deflation lumen extending to proximate the proximal end of the retrieval catheter. While applying suction at the proximal end of the aspiration lumen of the elongated shaft, the balloon may be inflated to partially restrict or fully occlude blood flow, thereby potentially increasing the suction pressure for extracting the debris. The balloon may then be deflated.

Next, the filter may be collapsed into a low profile state around the distal end of the filter retrieval catheter, and the catheter with the attached filter may be removed from the vasculature.

DETAILED DESCRIPTION OF THE INVENTION

The following detailed description should be read with reference to the drawings, in which like elements in different drawings are numbered in like fashion. Those skilled in the art will recognize that many of the examples provided could have suitable alternatives that may be utilized without departing from the spirit of the disclosed invention.

Figure 1:
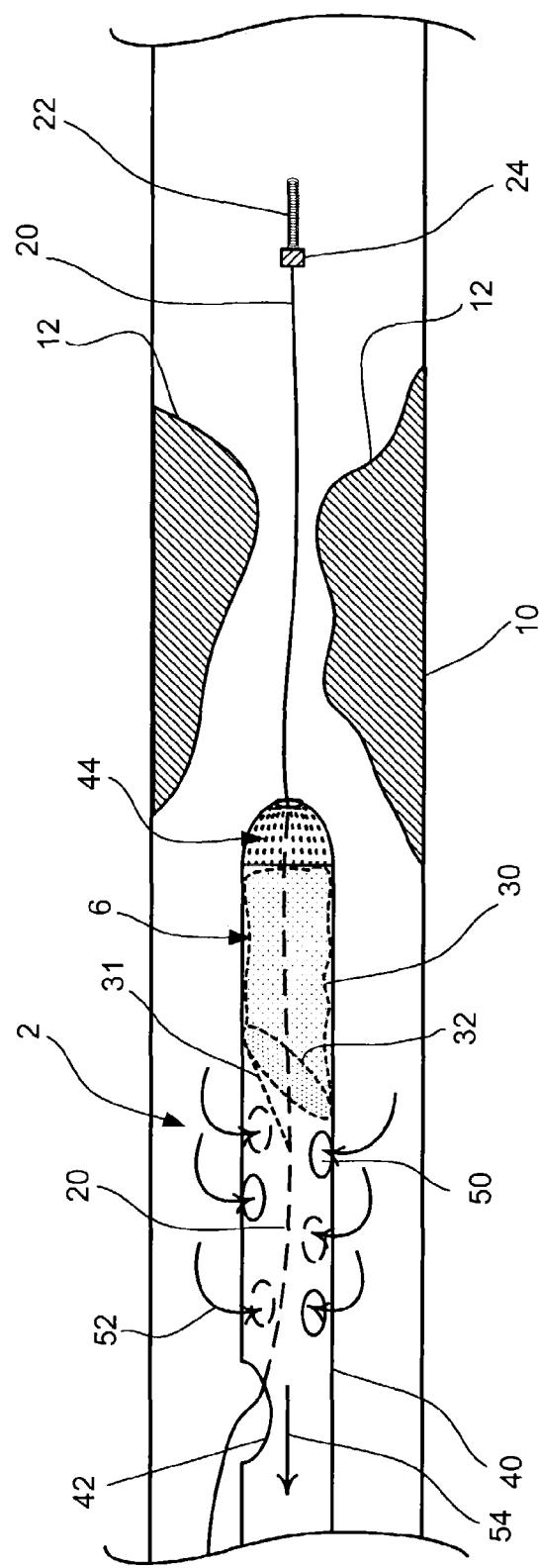
FIG. 1 is an illustration of an embodiment of an aspirating filter delivery catheter defining aspiration ports, a blood permeable filtration device, and an operable end cap.

FIG. 1 is an illustration of an aspirating filter delivery catheter 2 in accordance with an embodiment of the present invention. Delivery catheter 2 includes an elongated shaft 40 having a proximal end (not shown) and a distal end, and contains a filtration device 6. An operable end cap 44 may be disposed on the distal end of elongated shaft 40. As shown in FIG. 1, elongated shaft 40, filtration device 6 and operable end cap 44 of delivery catheter 2 could be slidably coupled to a guide wire 20 therethrough. Catheter 2 can include a side guide wire opening 42.

Using well known percutaneous techniques, guide wire 20, having a proximal end (not shown), a flexible distal tip 22 and a filter stop 24 fixedly attached to guide wire 20, may be manipulated into position within the lumen of a blood vessel 10. In FIG. 1, the inside wall of blood vessel 10 is shown having one or more lesions and/or stenosis 12, referred to as a target site 12, with guide wire distal tip 22 and filter stop 24 located distal of target site 12.

Elongated shaft 40 includes one or more aspiration ports 50 located circumferentially and/or longitudinally proximate the distal end of elongated shaft 40 and proximal of filtration device 6. As cap 44 passes distally through lesion 12, emboli may be dislodged. Such emboli may flow along paths 52 and enter elongated shaft 40 through aspiration ports 50. The emboli could then be extracted along path 54 by a suction providing means (not shown) fluidly connected to the proximal end (not shown) of elongated shaft 40.

Filtration device 6 may include a self-expanding support hoop 32 with a blood permeable sac 30 and a suspension member 31 attached thereto. The open end of blood permeable sac 30 may be affixed to support hoop 32 such that support hoop 32 forms a mouth through which blood may flow into blood permeable sac 30. Suspension member 31, when connected to support hoop 32 and guide wire 20, could be useful in holding self-expanding support hoop 32 and blood permeable sac 30 in an eccentrically and laterally displaced position relative to the direction of blood flow.

As shown in FIG. 1, operable end cap 44 may be attached to the distal end of elongated shaft 40. While advancing delivery catheter 2 toward and past target site 12, such as a stenosis or a lesion, operable end cap 44 may be retained in a closed state to limit emboli collection on the distal side of filtration device 6.

Figure 2A:
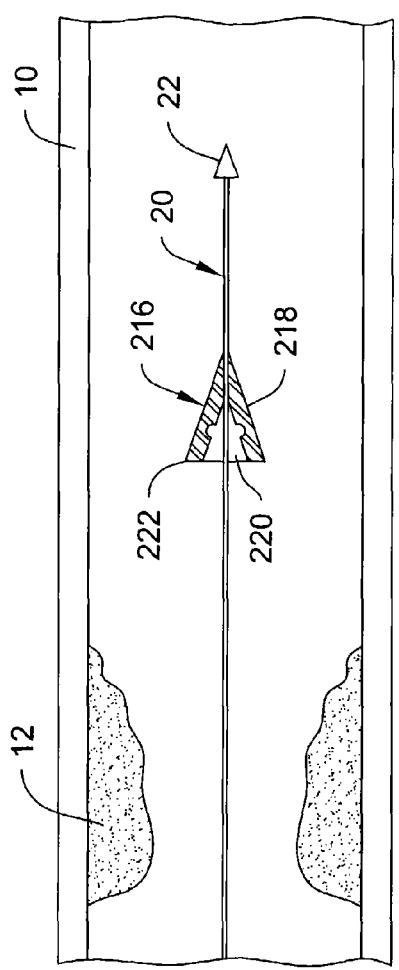
FIGS. 2A-2C illustrate an embodiment of a filter docking mechanism.
Figure 2B:
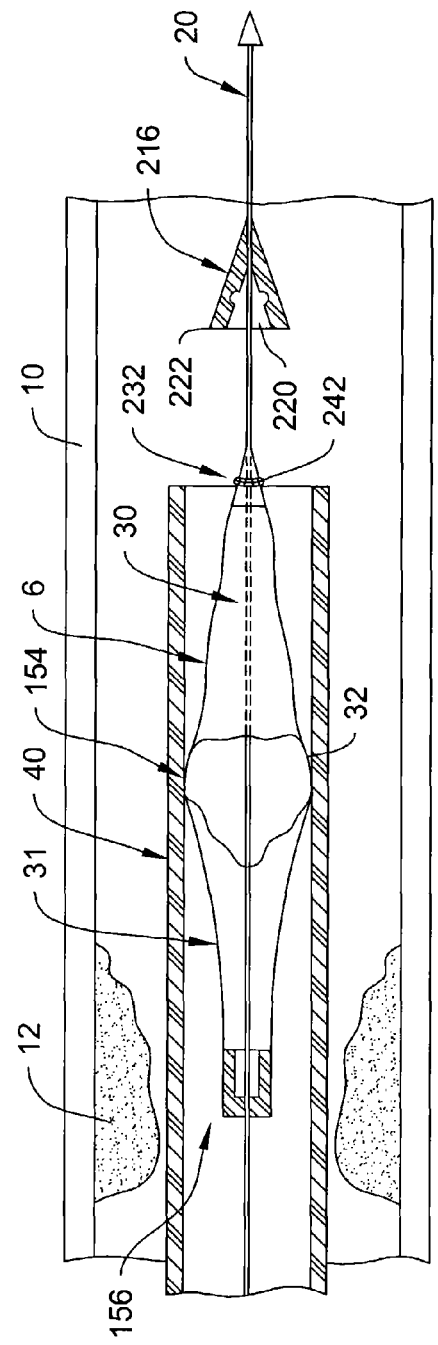
Figure 2C:
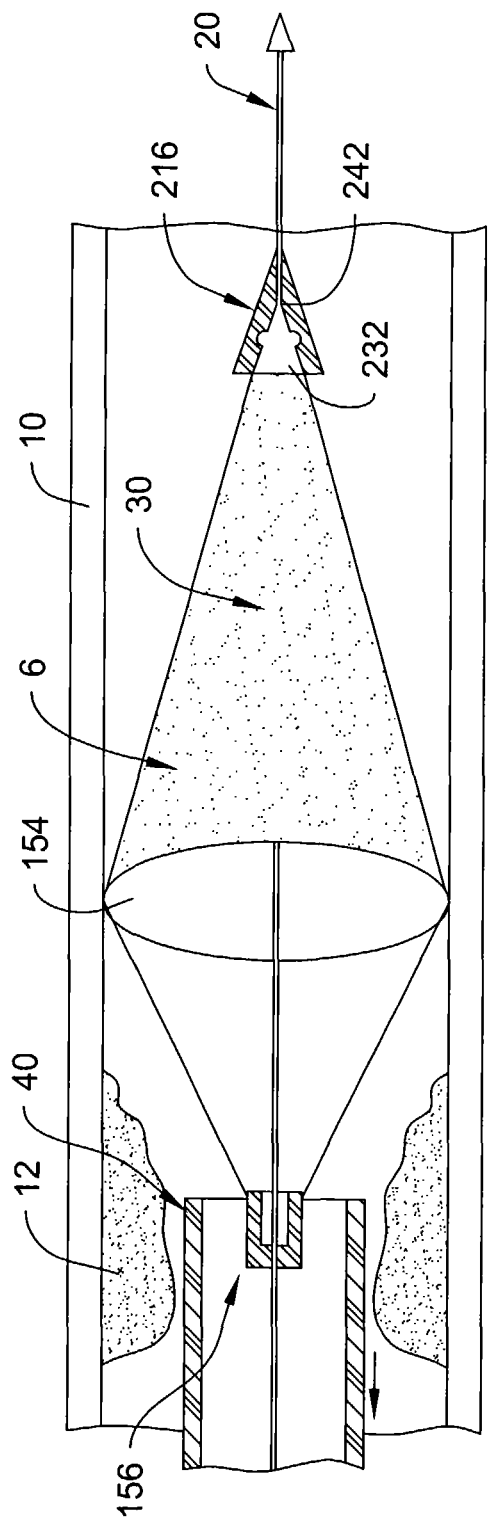

FIGS. 2A-2C illustrate an alternate embodiment of the present invention, wherein a filter docking member may be used instead of filter stop 24 with the distal side of filtration device 6 having a matched mating element. Examples of such filter docking members are disclosed in co-owned U.S. Pat. No. 6,152,946 to Broome et al., which is incorporated herein by reference.

As illustrated in FIG. 2A, guide wire 20, having spring coil tip 22, may also include filtration device docking member 216 coupled to a distal portion of guide wire 20. Docking member 216 may be rigidly coupled to guide wire 20, and in one embodiment, could be formed of a generally "V"-shaped member 218 including docking channel 220. Docking member 218 could include groove 222 opening to channel 220. Docking member 216, may be used to removably secure filtration device 6 thereto as explained in the following.

In one embodiment, docking member 216 may be permanently formed on guide wire 20. Alternatively, docking member 216 may be detachably connected to guide wire 20 such as by a friction fit between guide wire 20 and a channel (not shown) of docking member 216, or by a mechanical attachment mechanism. If detachable, docking member 216 may be used on any suitable guide wire, thereby adapting the guide wire for operation with filtration device 6.

FIG. 2B illustrates an embodiment of filtration device 6 which may be selectively coupled to docking member 216. Filtration device 6 may include distal cone 232, blood permeable sac (i.e., filter) 30, suspension member 31, support hoop 32, and collar 156. Cone 232 may be coupled to the distal end of filter 30. Cone 232 could be "V"-shaped and formed of a rigid member having a distal opening (not shown) sized for insertion of guide wire 20 therethrough. Cone 232 may include locking ring 242 extending about an outer perimeter of cone 232. Locking ring 242 could be sized for insertion into groove 222 of docking member 216.

Filter support hoop 32 may have a generally circular mouth 154 and a plurality of suspension members, i.e., suspension struts or ribs 31. Mouth 154 may support filter 30, and could be formed of a wire loop coupled thereto via a known biocompatible adhesive or other suitable means as are well known in the art. Filter mouth 154 may be coupled to collar 156 via suspension member 31 such that collar 154 could slide along guidewire 32 to deploy or retrieve filtration device 6. Suspension struts 31 may be attached to collar 156 and mouth 154 by any suitable means as are well known in the art. Filter frame 32, mouth 154, and suspension ribs 31 could be formed of a wire or strip of a relatively elastic material such as a Nitinol material.

In use, filtration device 6 may be mounted relative to guide wire 20 by inserting guide wire 20 through an opening in cone 232. Filtration device 6 could be advanced over guide wire 20 to align cone 232 with docking member 216. Cone 232 may be forced into channel 220 of docking member 216 until ring 242 snaps into groove 222 and is maintained therein. Filtration device 6 could be inserted in a low-profile collapsed condition via cooperation with sheath 40, and positioned at a treatment site, as comparatively illustrated in FIGS. 2B and 2C.

In another embodiment of the present invention, yet another filter stop or docking member may additionally be affixed on guide wire 20, and positioned proximal of collar 156.

In other embodiments, filtration device 6 may be coupled to a filter delivery wire (not shown) for deploying and retracting filtration device 6. To one of ordinary skill in the art, it is well known that numerous alternative embodiments for delivering and retrieving one or more filtration devices are also possible.

From the foregoing descriptions of various embodiments for affixing one or more filter stop or filter docking mechanism on to guide wire 20, it should be apparent that the movement of filtration device 6 may be restricted either in one direction, viz., distally or proximally, or in two directions, viz., both distally and proximally.

Figure 3:
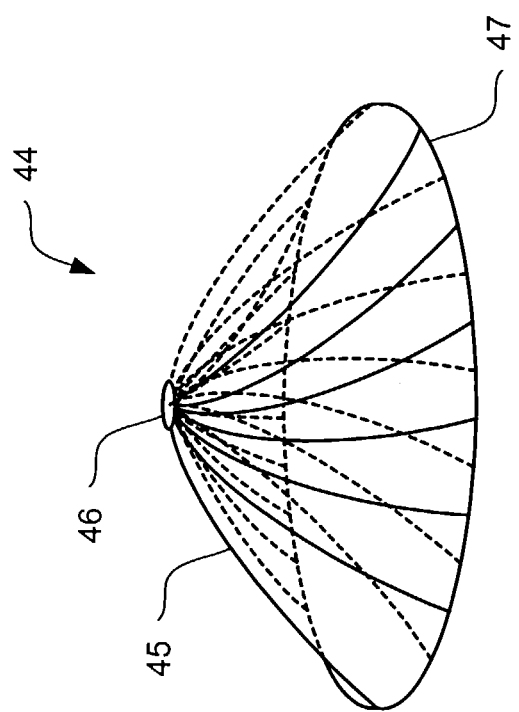
FIG. 3 is an illustration of an embodiment of an operable end cap.

FIG. 3 is an illustration of operable end cap 44 in accordance with one embodiment of the present invention. Operable end cap 44 may include a guide wire port 46, a plurality of interleaving plates 45, and a base 47. Guide wire port 46 could provide an access point through which delivery catheter 2 may be slidably coupled to guide wire 20. Interleaving plates 45 may be in the shape of, for example, a frustum of a cone, or a dome. Interleaving plates 45 may also be designed and constructed in a form such as petals in a flower bud. Base 47 of operable end cap 44 may be fixedly and flexibly attached to the distal end of elongated shaft 40.

It is advantageous for operable end cap 44 to be constructed such that it could be pushed into an open state by applying a relatively light force on the proximal side of interleaving plates 45 of end cap 44. End cap 44 could be opened either by pushing filtration device 6 in the distal direction, or by pulling elongated shaft 40 in the proximal direction, or by a combination thereof. Filtration device 6 may thus exit elongated shaft 40 through the now open operable end cap 44, and placed distal of target site 12 within the lumen of blood vessel 10. Upon exiting delivery catheter 2, self-expanding support hoop 32 may open radially to engage the inside wall of blood vessel 10.

Operable end cap 44 as illustrated in FIG. 3, and discussed in the foregoing, is one illustrative example for such devices. It should be apparent to one of ordinary skill in the art, that numerous additional shapes and mechanisms are possible for an operable end cap for providing the desired functionality.

Figure 4:
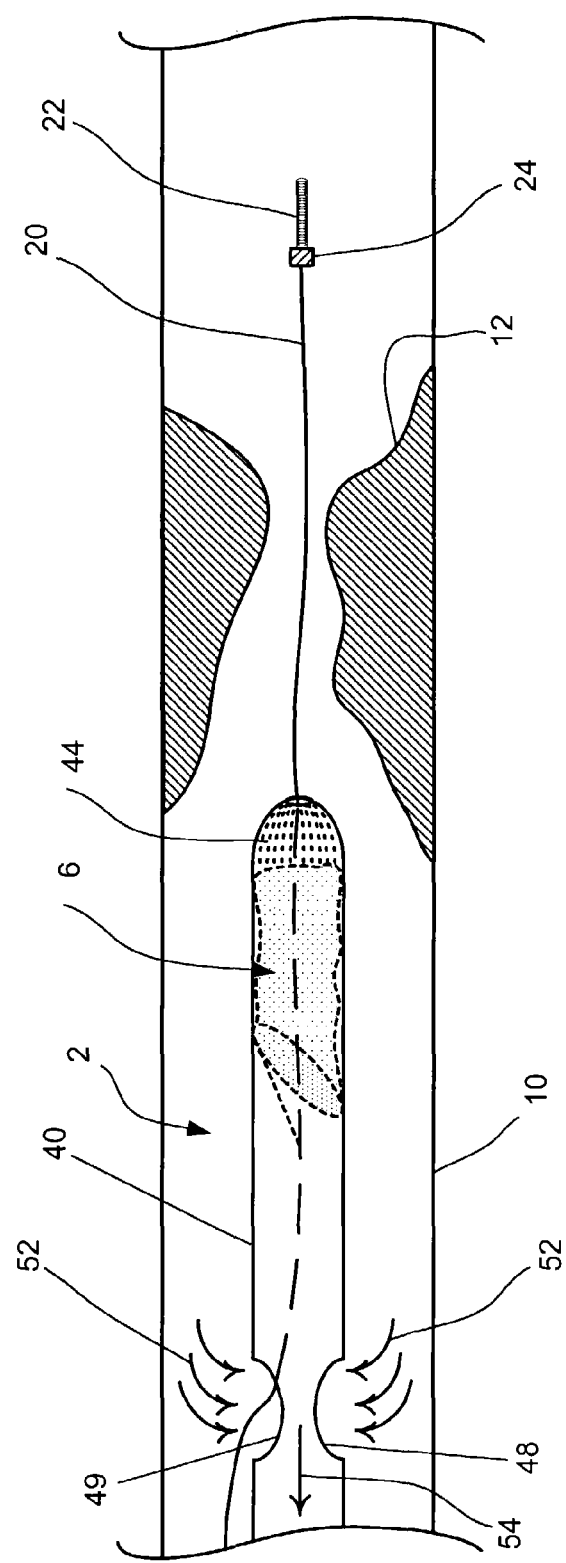
FIG. 4 is another embodiment of the aspirating filter delivery catheter of FIG. 1.

FIG. 4 is an illustration of an alternate embodiment of aspirating filter delivery catheter 2 of the present invention, wherein the placement and number of aspiration ports on elongated shaft 40 may differ from the design shown in FIG. 1. The embodiment in FIG. 4 shows that aspiration holes 48 and 49 may be located proximate the distal end of elongated shaft 40 and proximal of filtration device 6. Aspiration hole 49 may serve a dual purpose as a port for guide wire 20 and an entry port for the debris flowing along paths 52. Debris entering elongated shaft 40 through ports 48 and 49 may be extracted along flow path 54 by a suction providing means (not shown) fluidly connected to the proximal end (not shown) of aspirating filter delivery catheter 2. Although only two aspiration holes 48 and 49 are explicitly shown for the alternate embodiment in FIG. 4, it should be realized that a plurality of aspiration holes could be placed longitudinally and/or circumferentially on elongated shaft 40 proximal of filtration device 6.

Figure 5:
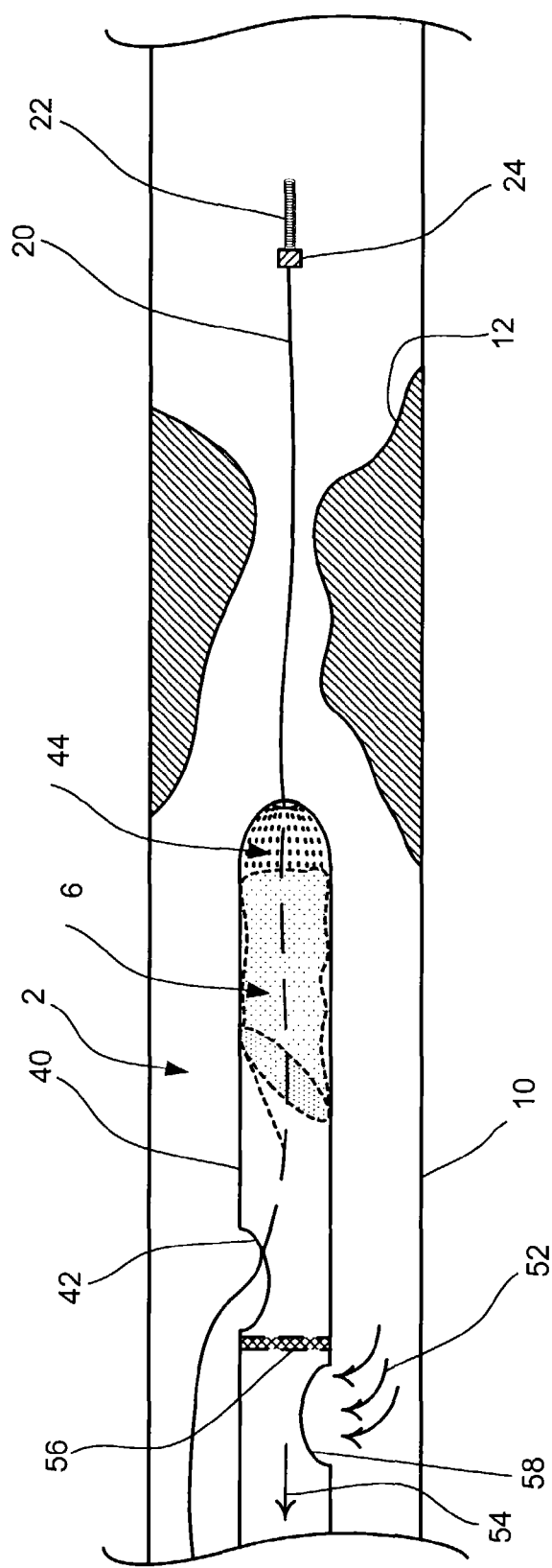
FIG. 5 is yet another embodiment of the aspirating filter delivery catheter of FIG. 1.

FIG. 5 shows yet another embodiment of aspirating filter delivery catheter 2 wherein a non-porous blocking wall or plug 56 may be fixedly located within the lumen of elongated shaft 40, proximal of guide wire port 42. The portion of elongated shaft 40 distal of blocking wall 56 could contain filtration device 6 and operable end cap 44. The portion of elongated shaft 40 proximal of blocking wall 56 may have an aspiration port 58 proximate blocking wall 56. Debris could enter elongated shaft 40 through aspiration port 58 along flow paths 52, and may then be extracted along flow path 54 by a suction providing means (not shown) fluidly connected to the proximal end (not shown) of delivery catheter 2. In FIG. 5, only one aspiration port 58 is explicitly shown for this alternate embodiment, however, it should be realized that a plurality of aspiration holes may be placed longitudinally and/or circumferentially on elongated shaft 40 proximal of blocking wall 56.

The foregoing descriptions of the various embodiments have focused around delivery lumen 2 as having one lumen for one or more purposes, viz., guide wire lumen, filter delivery lumen, and aspiration lumen. It should be apparent to those of ordinary skill in the art that delivery lumen 2 may include more than a single lumen, e.g., delivery lumen 2 may have two lumens, for example, one being a guide wire lumen, and the other being a filter delivery and aspiration lumen. Alternately, delivery lumen 2 may include three separate lumens: one being a guide wire lumen, another being a filter delivery lumen, and the other being an aspiration lumen, for example.

Described hereinafter is one of several methods in which aspirating filter delivery catheter 2 may be used in practice. One embodiment of a method of using delivery catheter 2 may include placement of guide wire 20, such that flexible distal tip 22 and filter stop 24 are positioned distally of target site 12 within the lumen of blood vessel 10. Next, aspirating filter delivery catheter 2 including filtration device 6 and operable end cap 44 may be slidably coupled to guide wire 20, and the distal end of delivery catheter 2 advanced toward target site 12.

When the distal end of delivery catheter 2 is proximate the proximal side of stenosis or lesion 12, a suction providing means may be fluidly coupled to the proximal end of elongated shaft 40. The lumen of elongated shaft 40 may provide fluid communication between aspiration ports 50 and the suction providing means. Delivery catheter 2 may be advanced in the distal direction for traversing target site 12, while suction is being administered for extracting, through aspiration ports 50, debris, emboli, thrombi, etc., resulting from the movement of delivery catheter 2.

Next, filtration device 6 may be deployed within the lumen of blood vessel 10 and distal of target site 12 by pushing filtration device 6 in the distal direction and/or pulling delivery catheter 2 in the proximal direction. Operable end cap 44 could be pushed open with filtration device 6 exiting the distal end of elongated shaft 40, and self expanding support hoop 32 may extend radially to engage the inside wall of blood vessel 10. Blood may now enter and flow through blood permeable sac 30, and aspirating filter delivery catheter 2 may be extracted from blood vessel 10.

An interventional device may be introduced over guide wire 20 to target site 12, and one or more vascular procedure such as angioplasty, atherectomy, thrombectomy, stent placement, etc., may be conducted for treating occlusive vascular disease. Any one of these procedures could cause material to dislodge from the inside wall of blood vessels and/or create thrombi, emboli, etc., into the bloodstream. With filtration device 6 deployed distally of stenosis or lesion 12, the debris may enter and get entrapped within blood permeable sac 30. After the procedure has been completed and interventional device removed, the emboli laden filtration device may also be extracted.

Blood permeable sac 30 may contain small and/or large amounts of debris of differing form, size, etc. Under certain circumstances it may be possible to use a conventional filter retrieval catheter to collapse and extract the filtration device from the vasculature with the debris encapsulated within blood permeable sac 30. However, under certain conditions blood permeable sac 30 might become occluded with debris making it relatively difficult to collapse and extract filtration device 6 using a conventional filter retrieval catheter and method. Therefore, there exists a need for an aspirating filter retrieval catheter for extracting, at least in part, some of the entrapped debris so that filtration device 6 may be collapsed for easy removal without releasing debris into the blood stream.

Figure 6:
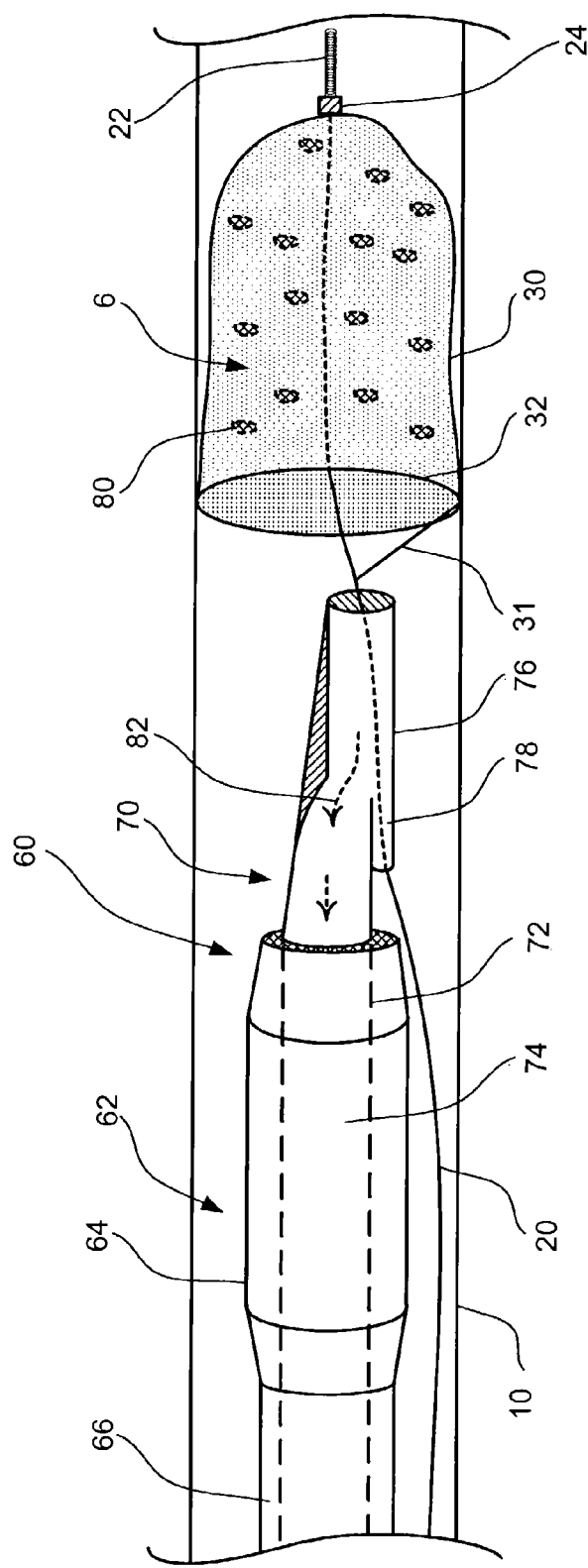
FIG. 6 is an illustration of an embodiment of an aspirating filter retrieval catheter defining an aspiration lumen, a guide wire lumen, and an inflatable/deflatable balloon.

FIG. 6 is an illustration of an aspirating filter retrieval catheter 60 in accordance with an embodiment of the present invention. Retrieval catheter 60 may include an elongated shaft 70 having a proximal end (not shown) and a distal end, and could also have an inflatable/deflatable balloon 62 proximate the distal end of elongated shaft 70.

Elongated shaft 70 may include an aspiration lumen 74 therethrough having a proximal end (not shown) and a distal end, and a guide wire lumen 78, also having a proximal end and a distal end, guide wire lumen 78 fixedly attached proximate the distal end of elongated shaft 70. The distal end of guide wire lumen 78 may be fluidly coupled to the distal end of aspiration lumen 74 such that both lumens 74 and 78 commonly form the opening at the distal end of elongated shaft 70. Guide wire lumen 78 may be used for slidably coupling retrieval catheter 60 to guide wire 20. The proximal end of aspiration lumen 74 may be fluidly coupled to a suction providing means (not shown) for extracting debris 80 from blood permeable sac 30.

Balloon 62, having an expanded state and a contracted state is disposed proximate of the distal end of elongated shaft 70. Balloon 62 could be configured such that in the expanded state, surface 64 thereof may engage the inner surface of the lumen of blood vessel 10. As shown in FIG. 6, elongated shaft 70 may be surrounded by inflation lumen 66. The proximal end (not shown) of lumen 66 may be fluidly coupled to a fluid source, and the distal end of lumen 66 may be in fluid communication with balloon 62 through an orifice such that lumen 66 may be used for injecting and/or removing fluid from balloon 62, as is well known in the art, for the purpose of inflating and/or deflating balloon 62. Blood flow within vessel 10 may be partially restricted and/or fully occluded by expanding and/or contracting balloon 62 during any portion of the interventional procedure and as deemed necessary or advantageous to do so.

Described hereinafter is one of several methods by which aspirating filter retrieval catheter 60 may be used in practice. One embodiment of a method of using retrieval catheter 60 may include slidably coupling retrieval catheter 60 to guide wire 20 via guide wire lumen 78. Retrieval catheter 60 may be manipulating within the lumen of blood vessel 10 to place the distal end at a position proximate where suspension strut 31 attaches to guide wire 20.

A suction providing means (not shown) may be fluidly coupled to the proximal end of aspiration lumen 74 (i.e., elongated shaft 70 or retrieval catheter 60) for possibly inducing suction pressure at the distal end. Suction may be started, and debris 80 entrapped within blood permeable sac 30 could be extracted through aspiration lumen 74 along flow path 82.

Under certain circumstances, blood permeable sac 30 may be debris laden such that additional suction pressure may be required for extracting debris 80. In such cases, balloon 62 may be inflated to partly restrict or fully occlude blood flow, thereby enabling an increase in the suction pressure in the region proximate self expanding support hoop 32, and enhancing extraction of debris 80. Suction may either be continuously applied or stopped while filtration device 6 is collapsed to a low profile state and extracted from the vasculature.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

We claim:

1. A filter delivery catheter, comprising:
   an elongated shaft defining a shaft lumen, the shaft having a proximal end and a distal end;
   the elongated shaft including a plurality of aspiration ports;
   the plurality of aspiration ports located circumferentially on the elongated shaft at one or more longitudinal positions proximal of the distal end; and
   a blood permeable filtration device for trapping debris within the lumen of a blood vessel, the filtration device having a proximally-facing mouth, an expanded configuration, and a collapsed configuration, the filtration device in its collapsed configuration being sized to fit within the shaft lumen;
   wherein all of aspiration ports are located proximally of the filtration device when the filtration device is entirely contained within the shaft lumen;
   wherein the distal end of the elongated shaft further comprises an operable end cap fixedly attached thereto.

2. The filter delivery catheter of claim 1, wherein the filtration device is enclosed within the elongated shaft proximal of the operable end cap and proximate the distal end of the elongated shaft.

3. The filter delivery catheter of claim 1, wherein the plurality of aspiration ports are located on the elongated shaft proximate the distal end of the elongated shaft and proximal of the filtration device.

4. The filter delivery catheter of claim 3, wherein the plurality of aspiration ports are located longitudinally on the elongated shaft.

5. The filter delivery catheter of claim 1, wherein the lumen of the elongated shaft fluidly couples the plurality of aspiration ports to the proximal end of the elongated shaft.

6. The filter delivery catheter of claim 1, wherein the proximal end of the elongated shaft is in fluid communication with a suction providing means for extracting debris from the lumen of the blood vessel through the plurality of aspiration ports.

7. The filter delivery catheter of claim 1, wherein the filtration device is located within the elongated shaft proximate the distal end of the elongated shaft.

8. The filter delivery catheter of claim 1, wherein the plurality of aspiration ports are located proximate the distal end of the elongated shaft.

9. The filter delivery catheter of claim 1, wherein the filtration device is a floating filter.

10. The filter delivery catheter of claim 1, wherein the filtration device is fixedly attached to a wire.

11. The filter delivery catheter of claim 1, wherein the debris includes one or more of emboli, thrombi, and dislodged tissue.

12. A filter delivery catheter, comprising:
    an elongated shaft defining a shaft lumen, the shaft having a proximal end and a distal end;
    the elongated shaft including a plurality of aspiration ports;
    the plurality of aspiration ports located circumferentially on the elongated shaft at one or more longitudinal positions proximal of the distal end;
    a blood permeable filtration device for trapping debris within the lumen of a blood vessel, the filtration device having a proximally-facing mouth, an expanded configuration, and a collapsed configuration, the filtration device in its collapsed configuration being sized to fit within the shaft lumen; and
    a guidewire slidably disposed within the shaft lumen;
    wherein all of the aspiration ports are located proximally of the filtration device when the filtration device is entirely contained within the shaft lumen;
    wherein the guidewire passes through the proximal most aspiration port.

13. The filter delivery catheter of claim 1, further comprising a guidewire passing through the proximal most aspiration port.

14. The filter delivery catheter of claim 1, wherein the end cap includes a plurality of interleaving plates.

15. The filter delivery catheter of claim 14, wherein the plurality of interleaving plates form a cone shape.

16. The filter delivery catheter of claim 14, wherein the plurality of interleaving plates form a dome shape.

* * * * *